(12) United States Patent
Hara et al.

(10) Patent No.: US 6,294,703 B1
(45) Date of Patent: Sep. 25, 2001

(54) PROCESS FOR THE MANUFACTURE OF CYCLOALKYLDIMETHANOL

(75) Inventors: Yoshinori Hara; Koetsu Endou; Hiroko Takahashi, all of Yokohama (JP)

(73) Assignee: Mitsubishi Chemical Company, Tokyo (JP)

( * ) Notice: Subject to any disclaimer, the term of this patent is extended or adjusted under 35 U.S.C. 154(b) by 0 days.

(21) Appl. No.: 09/337,521

(22) Filed: Jun. 22, 1999

(30) Foreign Application Priority Data

Jun. 22, 1998 (JP) .................................................. 10-174386
Aug. 11, 1998 (JP) .................................................. 10-226818

(51) Int. Cl.$^7$ .................................................. C07C 31/13
(52) U.S. Cl. .............................................. 568/831; 502/25
(58) Field of Search ................................................ 568/831

(56) References Cited

U.S. PATENT DOCUMENTS

| 5,334,779 | | 8/1994 | Kuo . | |
| 5,426,246 | * | 6/1995 | Nagahara | 568/831 |
| 5,969,194 | * | 10/1999 | Hara | 568/700 |
| 6,018,048 | * | 1/2000 | Morikawa | 546/185 |

FOREIGN PATENT DOCUMENTS

| 6-228028 | | 8/1994 | (JP) . |
| 7-165644 | | 6/1995 | (JP) . |
| 10-15388 | * | 1/1998 | (JP) . |
| 11-147845 | * | 6/1999 | (JP) . |
| 11-255684 | * | 9/1999 | (JP) . |

OTHER PUBLICATIONS

Encyclopedia of Chem. Tech., Kirk–Othmer, vol. 12, $4^{th}$ ed., pp. 732–737, 1994.

* cited by examiner

Primary Examiner—Michael L. Shippen
(74) Attorney, Agent, or Firm—Oblon, Spivak, McClelland, Maier & Neustadt, P.C.

(57) ABSTRACT

A process for making cycloalkyldimethanol, includes hydrogenating at least one cycloalkyldicarboxylic acid and/or an alkyl ester thereof with a catalyst, to produce a cycloalkyldimethanol, where the catalyst contains ruthenium, tin and platinum. Also, a method for regenerating a used catalyst, includes contacting the used catalyst with a base, where the catalyst includes ruthenium, tin and platinum.

18 Claims, 2 Drawing Sheets

PROCESS FOR THE MANUFACTURE OF CYCLOALKYLDIMETHANOL

BACKGROUND OF THE INVENTION

1. Field of the Invention

The present invention relates to a process for the manufacture of cycloalkyldimethanol by a direct hydrogenation of a starting compound selected from cycloalkyldicarboxylic acid and an alkyl ester compound thereof and, more particularly, it relates to a process for the manufacture of 1,4-cyclohexanedimethanol (hereinafter, referred to as 1,4-CHDM) from a starting compound selected from 1,4-cyclohexanedicarboxylic acid and an alkyl ester compound thereof. Further, the present invention relates to a method for regeneration of a catalyst and to a process of hydrogenation using the regenerated catalyst.

2. Discussion of the Background

Cycloalkyldimethanol such as 1,4-CHDM is useful in polyester paints and in synthetic fibers and synthetic resins of a polyester type and is used particularly as a material for resins and fibers having excellent thermal resistance, weather resistance, physical strength, etc. (Encyclopedia of Chem. Tech., Kirk-Othmer, Vol. 12, 4th. ed., pp.732–737 (1994), incorporated herein by reference).

In the past 1,4-CHDM has been made by a process in which dimethyl terephthalate is subjected to hydrogenation using a catalyst of Ru or Pd carried on alumina to give dimethyl cyclohexanedicarboxylate, and then a side chain of the resulting ester is subjected to a hydrogenation reaction in the presence of a Cu—Zn oxide catalyst, to manufacture 1,4-CHDM, as mentioned, for example, in JP-W-8-510686. In addition, in JP-A-6-228028 is described a process for the manufacture of 1,4-CHDM where dialkyl terephthalate is subjected to hydrogenation to give dimethyl 1,4-cyclohexanedicarboxylate, and then the side chain of the product is hydrogenated using a catalyst containing Ru and Sn to manufacture 1,4-CHDM.

On the other hand, with regard to a process for direct hydrogenation of an aliphatic carboxylic acid or carboxylic acid ester, methods where a catalyst containing ruthenium, platinum and tin have been proposed. For example, JP-A-7-165644 describes a method for the manufacture of 1,4-butanediol and tetrahydrofuran by hydrogenation of maleic acid and succinic acid; JP-A-10-175897 describes a method for the manufacture of 3-hydroxymethyl-1,6-hexanediol by hydrogenation of 1,2,4-butanetricarboxylic acid; and JP-A-10-306047 describes a method for the manufacture of 1,6-hexanediol by hydrogenation of a mixture of carboxylic acid and carboxylate including adipic acid and hydroxycaproic acid. In these references, there is no description of hydrogenation reactions of alicyclic carboxylic acids and, in addition, there is no description at all for a method of regenerating of a ruthenium catalyst having a reduced activity. The alicyclic carboxylic acids (which is a starting compound used in the present invention) has a structure having more steric hindrance than the aliphatic carboxylic acids which has been used as a starting compound. Therefore, the conventional known catalysts are not always applicable or it is predicted that the reactivity is reduced in the case of alicyclic carboxylic acids as compared with aliphatic carboxylic acids.

In the process of JP-W-8-510686, there are the disadvantages that an esterifying step is essential, since an ester is used as the starting material, and that relatively severe reaction conditions such as high temperatures and high pressures are used since a copper catalyst is used for hydrogenation of the side chain. The process of JP-A-6-228028 is not so satisfactory from an industrial view, in terms of the yield of 1,4-CHDM.

In methods where a ruthenium catalyst is used, ruthenium is expensive and, therefore, it is important to carry out such a process on an industrial scale so that not only is the activity of the catalyst retained for a long period of time, but also the catalyst having reduced activity is regenerated. Further, although 1,4-CHDM is usually obtained as a mixture of trans- and cis-compounds, polyester resins manufactured from trans-1,4-CHDM have superior properties and, accordingly, there has been a demand for increasing the ratio of the trans-compound in the product.

SUMMARY OF THE INVENTION

The present inventors have intensively investigated the above-mentioned problems and, as a result, they have found that dissolution of the catalytic components can be suppressed and, in addition, cycloalkyldimethanol can be manufactured in high yield by a reaction with hydrogen in a liquid phase in the presence of a catalyst containing a combination of specific catalytic components, when the hydrogenation reaction of the side chain is carried out using an alicyclic carboxylic acid, such as cycloalkyldicarboxylic acid or an alkyl ester thereof as a starting compound. They have further found that activity of the catalyst is efficiently recovered when the catalyst which is used for the hydrogenation reaction and shows a reduced activity is treated by a specific method and, as a result thereof, the present invention has been accomplished.

Thus, the present invention includes a process for the manufacture of cycloalkyldimethanol, where at least one starting compound selected from cycloalkyldicarboxylic acid and an alkyl ester compound thereof is hydrogenated in a liquid phase using a catalyst containing the catalytic components of at least ruthenium, tin and platinum.

The present invention includes a method for the regeneration of a catalyst, where the catalyst containing the catalytic components of at least ruthenium, tin and platinum used in a hydrogenation reaction is treated with a solution containing a base.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
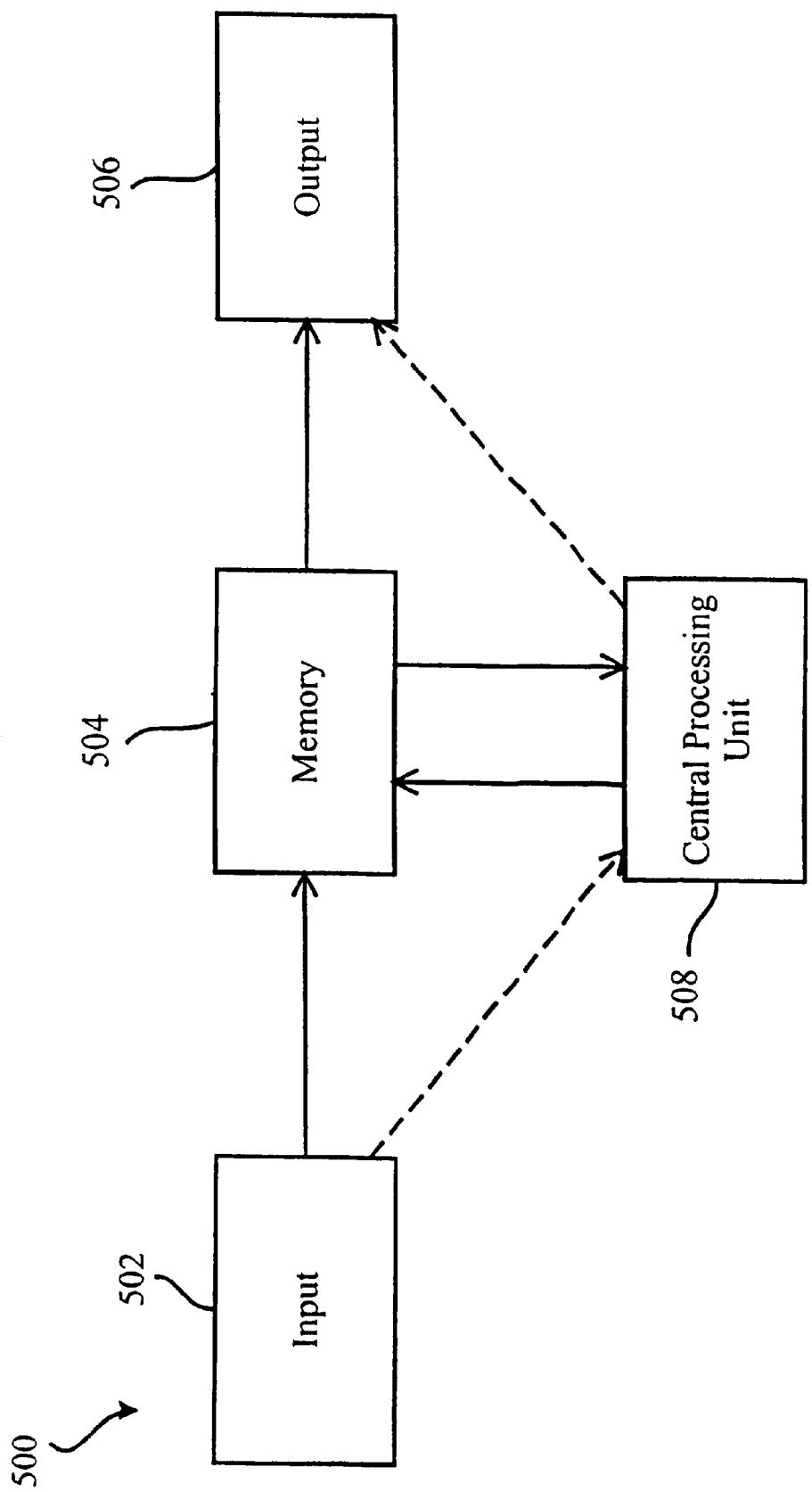
FIG. 1 illustrates an exemplary portion of a generalized computer system upon which portions of the invention may be implemented.

The starting compound which is used for the manufacture of the cycloalkyldimethanol in the present invention is at least one compound selected from cycloalkyldicarboxylic acid and an alkyl ester compound thereof. Carbon numbers of the cycloalkyl group in the cycloalkyldicarboxylic acid are preferably from 3 to 12 or, more preferably, from 3 to 8. The use of 1,4-cyclohexanedicarboxylic acid where the carbon numbers of the cycloalkyl group is 6, or an alkyl ester thereof, as a starting compound is most preferred because the product can be manufactured in high yield and the dissolution ratio of the catalytic components is reduced. When alkyl cycloalkyldicarboxylate is used as a starting compound, it is preferred to use a starting compound where the alkyl group for the alkyl ester has preferably 1–6 carbon atoms or, more preferably, 1–3 carbon atoms, such as an ester compound of methanol, ethanol and cyclohexanedicarboxylic acid. Those starting compounds may be used either solely or as a mixture. It is particularly preferred from an economical view to use cycloalkyldicarboxylic acid as a starting compound rather than an alkyl ester, because esterification is not necessary.

Among the cycloalkyldicarboxylic acids used as a starting compound, 1,4-cyclohexanedicarboxylic acid can be manufactured as a mixture of trans- and cis-isomers by hydrogenation of terephthalic acid in an aqueous solvent using a metal of group VIII, such as palladium or ruthenium, as a catalyst as mentioned, for example, in JP-A-58-198439.

The catalyst used in the hydrogenation reaction of the present invention is a catalyst containing at least ruthenium, tin and platinum as active components of the catalyst and, as a result of combination of those three components, the desired product can be manufactured in a high yield and, in addition, the dissolution of the catalytic components can be suppressed. Especially in the case of addition of platinum, it has been found that the catalytic activity is significantly improved and dissolution of the tin component is suppressed. Usually, these catalytic components are used in the metallic state and it is preferred to use the catalyst carried on a carrier. With regard to the carrier, porous carriers or oxide carriers, such as carbon, alumina, silica, diatomaceous earth, zirconia and titania may be used and, among them, the use of carbon, particularly activated carbon, is preferred because of its inertness to the reaction. Incidentally, two or more carriers may be used together.

Applying the catalyst onto the carrier may be conducted by any method which has been commonly used for the preparation of a carried catalyst, such as dipping, ion exchanging, or impregnating. Among them, the particularly easy, convenient and preferred method is dipping. In the case of a dipping method, a compound of a metal component to be carried is dissolved in a solvent such as water to prepare an aqueous solution of the metal compound, and then a carrier is dipped into the aqueous solution so that the metal component is carried on the carrier.

There is no particular limitation for the order of applying each of the metal components onto the carrier. All metal components may be applied at the same time or each of the components may be applied separately. However, in view of simplicity and convenience of operation, it is preferred to apply all metal components at the same time. If desired, each of the components may be applied separately, multiple times.

Incidentally, in the case of a catalyst where no carrier is used, the catalyst may be prepared by a coprecipitating method or by a method where reduction is conducted using a reducing agent as mentioned in C. S. Narasimhan, *Journal of Catalyst*, 121, 1, 165 (1990).

With regard to a compound of each catalytic metal component used for preparing the catalyst, it may be chosen based upon the method for preparing the catalyst but, usually, mineral acid salts such as nitrate, sulfate or chloride are used. In addition, organic acid salts such as acetate, hydroxide, oxide, or organometallic compound and complex salt, may be used as well and, among them, the use of chloride is particularly preferred. When the metal component is carried on a carrier, it is dried and then burned and reduced, as necessary, to give a catalyst.

Drying may usually be conducted by keeping in vacuo or passing dry gas over the material, such as air, at the temperature of not higher than 200° C. or, preferably, 50–150° C. When applying the catalytic metal components separately multiple times, the component is preferably dried whenever it is applied. Burning may usually be conducted by passing over the material air, nitrogen or the like at the temperature of 100–600° C or, preferably, 200–500° C. Reduction may be conducted either by a liquid phase reduction or by a gas phase reduction. Usually, hydrogen or methanol is used as a reducing gas and a gas phase reduction is conducted at 100–600° C. or, preferably, at 200–500° C.

The amount of each of ruthenium, tin and platinum carried is 0.5–50% by weight or, preferably, 1–20% by weight, as a metal. It is preferred that the molar ratio of tin to ruthenium (Sn:Ru) in the catalyst is 0.3–10:1 or, more preferably, 0.5–5:1. The molar ratio of platinum to ruthenium (Pt:Ru) in the catalyst is preferably 0.05–2.5:1 or, particularly preferably, 0.1–0.4:1.

In the present invention, hydrogenation of the starting compound is carried out in a liquid phase using a catalyst containing the catalytic components containing at least ruthenium, tin and platinum as mentioned above. Although hydrogenation in the present invention may be carried out without a solvent, it is usually conducted in the presence of a solvent. With regard to the solvent, water, an alcohol, such as methanol or ethanol, an ether, such as tetrahydrofuran or dioxane, or a hydrocarbon, such as hexane or decalin, is usually used either solely or as mixtures if necessary. The use of an aqueous solvent including water is particularly preferred in the present invention. The amount of solvent used to the starting compound is usually from 0.1- to 20-fold by weight or, preferably, from 1- to 10-fold by weight. The amount of water in the solvent is preferably from 20- to 100-fold by weight or, more preferably, from 50- to 100-fold by weight, based on the non-water components of the solvent.

When the reaction is carried out in the presence of one or more alkali metal salts and/or alkali earth metal salts in a liquid phase during the hydrogenation reaction, it is possible to improve the yield of a trans-compound in the product, such as 1,4-CHDM. Specific examples of alkali metal salts and alkali earth metal salts which are applicable in the present invention are salts of sulfuric acid, carbonic acid, oxalic acid, etc. and hydroxides, etc. of lithium, sodium, magnesium, calcium, etc. Among these, the use of sodium sulfate, calcium hydroxide or potassium hydroxide is preferred because they decrease the hydrogenating activity less, and improve the yield of the trans-compound in the product, such as 1,4-CHDM. When the amount of the alkali metal salt or alkali earth metal salt used is too small, the ratio of production of the trans-compound is reduced while, when too much is used, the hydrogenating activity is reduced. Therefore, the salts are preferably used in an amount of 0.1–80% by weight or, more preferably, 0.5–20% by weight, to the starting compound used.

With regard to the mode of using the alkali metal salts and/or the alkali earth metal salts, the salts may be added in powder form to the liquid phase for the hydrogenation reaction, or may be dissolved in water followed by adding thereto. With regard to the time for adding to the liquid phase, it is preferred that the salts are added to the liquid phase before starting the hydrogenation reaction.

The hydrogenation reaction of the present invention is usually carried out under pressurized hydrogen gas. The reaction is usually carried out at temperature of 50–350° C., preferably 100–260° C. or, particularly preferably, at 150–240° C. and at a pressure of 0.1–30 MPa or, preferably, at 1–25 MPa. The hydrogenation reaction may be carried out using a continuous method or a batch method and, in view of simplicity, convenience and economy of the operation, a continuous method is preferred. With regard to the reaction type, any of a liquid phase suspending reaction and a fixed bed flow reaction may be adopted and, in view of ease of separation of the catalyst, a fixed bed flow reaction is preferred.

From the reaction solution after completion of the reaction, the catalyst is separated by a solid-liquid separation, if necessary, and then the cycloalkyldimethanol is recovered by distillation, for example. Unreacted starting compounds, intermediates, etc. in the reaction solution, such as an ester of 1,4-CHDM with the starting compound can be recovered and recycled as the starting compound for the hydrogenation reaction.

After the hydrogenation reaction, the catalyst has a reduced activity, and may be regenerated by treating with a base. Examples of the base which may be used therefor are alkali metal hydroxide, carbonate or bicarbonate, or ammonia, ammonium carbonate or ammonium bicarbonate, or mixtures thereof. Specific examples of the alkali metal hydroxide, carbonate and bicarbonate are lithium hydroxide, sodium hydroxide, potassium hydroxide, cesium hydroxide, lithium carbonate, sodium carbonate, potassium carbonate, cesium carbonate, lithium bicarbonate, sodium bicarbonate, potassium bicarbonate and cesium bicarbonate. Among them, an alkali metal hydroxide or ammonia is preferred.

When such a base is dissolved in water or an aqueous solvent such as aqueous acetone or aqueous ether, and the catalyst is washed with the resulting aqueous solution, the activity of the catalyst can be effectively recovered. The concentration of the base for this treatment is usually 0.001–20N or, preferably, 0.01–5N. The amount of the solution used, to the catalyst to be regenerated, is usually 1–1000% by weight or, preferably, 2–500% by weight.

There is no particular limitation for contacting the catalyst with the solution containing the base and, for example, in the case of a suspension reaction, a method where the used catalyst is just taken out and added to a solution containing the base, followed by stirring may be used. In the case of a fixed bed reaction, a solution of the base may be supplied to a reactor filled with the catalyst. There is no particular limitation for the treating temperature so long as it will not adversely affect the catalyst. In view of the treating efficiency however, preferably the temperature is 25–150° C. or, more preferably, 25–100° C. When the treating time is too short or too long, the treating efficiency lowers and, therefore, treatment time is preferably 1–120 minutes or, more preferably, 5–30 minutes.

Although details of the effect of treating with the base is not clear, it is presumed that the derivatives of the starting carboxylic acid or carboxylate attach to the catalyst, and are washed out with the base whereby the catalytic activity is improved. Accordingly, the effect of treating with the base is achieved independent of the type of substrate. After treatment with a solution containing the base, the catalyst is washed with water and can be recycled to the hydrogenation reaction. Incidentally, with regard to a method for the hydrogenation reaction in case the reaction is conducted again, the same condition and reaction system as mentioned already may be adopted.

The present invention includes a computer program product which is a storage medium including instructions which can be used to program a computer or a plurality of networked computers to drive a device or devices to perform a process of the invention. The storage medium can include, but is not limited to, any type of disk including floppy disks, optical discs, CD-ROMs, and magneto-optical disks, ROMs, RAMs, EPROMs, EEPROMs, magnetic or optical cards, or any type of media suitable for storing electronic instructions.

The computer program product drives a device or devices for implementing the invention. This device, or these devices, are known to those of ordinary skill in the art, and include standard unit operation, as well as other devices, for examples those devices appropriate for carrying out these processes described in *Riegel's Handbook of Industrial Chemistry*, 8th ed. (1983); *Chemical and Process Technology Encyclopedia* (1974); and *Heterogeneous Catalysis in Practice*, McGraw-Hill Chemical Engineering Series (1980); appropriate portions of these references are hereby incorporated by reference.

FIG. 1 illustrates an exemplary portion of a generalized computer system 500 upon which portions of the invention may be implemented. For example, the configurations of the invention may each be implemented by a plurality of computers having a generalized configuration as exemplified by FIG. 1 or by a plurality of computers having configurations similar to those of FIGS. 1 and 2 described below.

An input 502 of FIG. 1 communicates with a memory 504 and a Central Processing Unit 508. The Central Processing Unit 508 communicates with the memory 504 and an output 506. The output 506 is also in communication with the memory 504. The Central Processing Unit 508 may include an arithmetic/logic unit and a control unit in the form of hardware and/or software (not shown). One or more of inputs 502 may each be in communication with one or more memories 504 and/or Central Processing Units 508. One or more Central Processing Units 508 may be in communication with one or more outputs 506 and/or memories 504 and/or inputs 502. One or more memories 504 may be in communication with one or more inputs 502 and/or Central Processing Units 508 and/or outputs 506. Clearly, a plurality of variations of computer hardware configurations may be realized in a network of computer systems upon which portions of the invention may be implemented.

Figure 2:
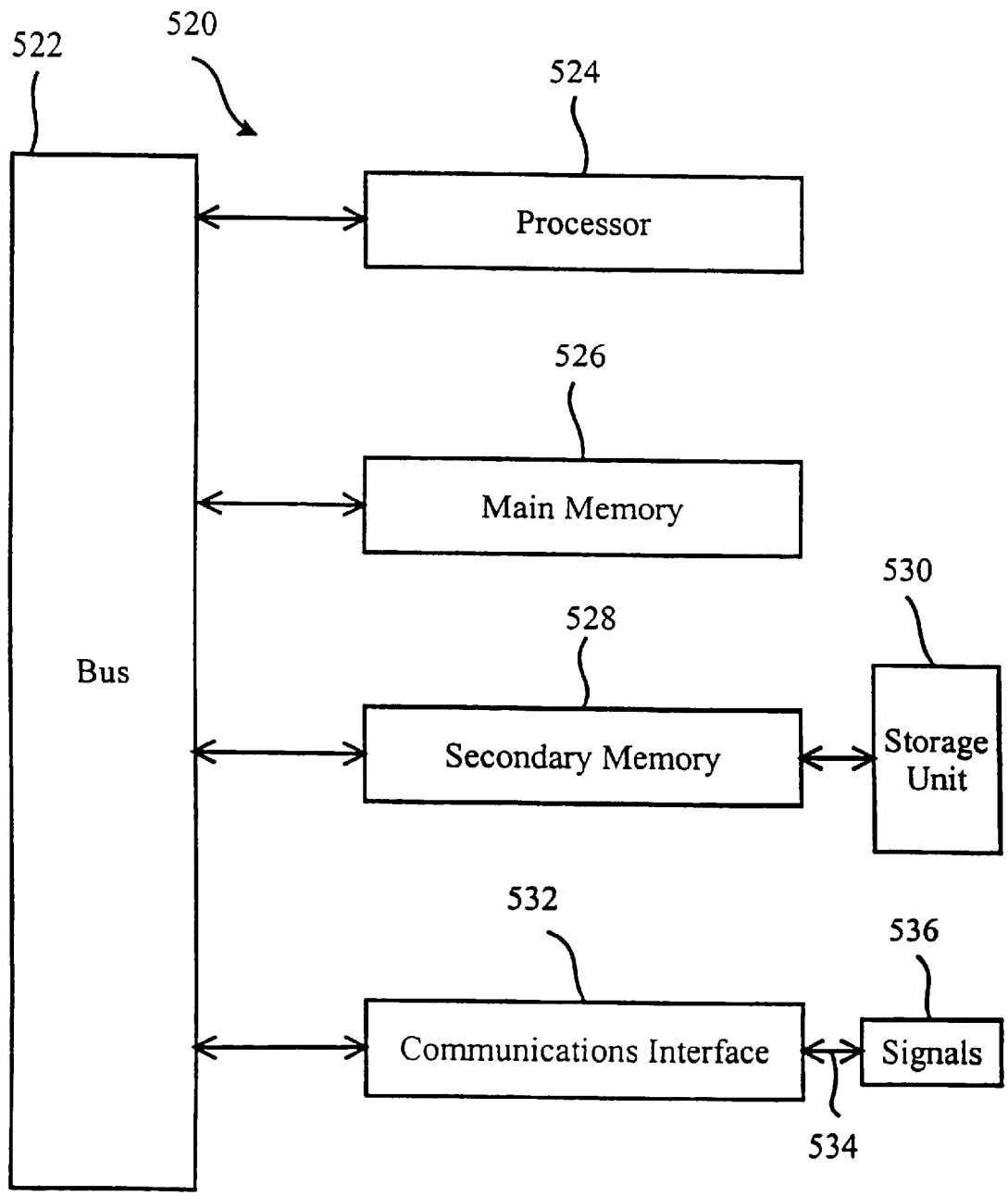
FIG. 2 illustrates an exemplary portion of a generalized hardware configuration, in the format of a workstation, upon which portions of the invention may be implemented.

FIG. 2 illustrates an exemplary hardware configuration of a generalized computer system 520 upon which portions of the invention may be implemented. One or more processors 524 are connected to a communication bus 522. The communication bus 522 also communicates with a main memory 526, preferably a random access memory ("RAM"). A secondary memory 528 communicating with the communication bus 522 may also be included in the computer system 520. The secondary memory 520 may include, for example, a hard disk drive, a removable storage drive such as a floppy disk drive, a magnetic tape drive, an optical disk drive, a program cartridge and cartridge interface, a removable memory chip (e.g., EPROM, PROM, ROM), or any other similar storage medium. The secondary memory 528 may be in communication with a storage unit 530 such as a floppy disk, magnetic tape, optical disk, or other storage medium read by and written to by a secondary memory device. The storage unit 530 includes a computer usable storage medium for storing computer software and data.

The computer system 520 may also include a communications interface 532 in communication with the communication bus 522 for transferring software and data between the computer system 520 and external devices. Examples of communications interfaces 532 include a modem, a network interface (e.g., a network card), a communications port, a PCMCIA slot and card, and other similar interfaces. Software and data transferred via the communications interface 532 are in the form of signals 536 which are provided to the communications interface 532 via a channel 534. The signals 536 may be electronic, electromagnetic, optical or other signals capable of being received by the communications interface 532. The channel 534 may be implemented using wire, cable, fiber optics, a phone line, a cellular phone link, an RF link or other communications channels.

Computer programs are stored in main memory 526 and/or secondary memory 528. Computer programs may be received via the communications interface 532. Computer programs, when executed by the processor 524, enable the computer system 520 to perform the features of the present invention.

This invention may be conveniently implemented using a network of conventional general purpose digital computers and/or microprocessors programmed according to the teachings of the present specification, as will be apparent to those skilled in the computer art from reading the above descriptions regarding the figures. Appropriate software coding can readily be prepared by skilled programmers based on the teachings of the present disclosure, as will be apparent to those skilled in the software art. The invention may also be implemented by the preparation of application specific integrated circuits or by interconnecting an appropriate network of conventional component circuits, as will be readily apparent to those skilled in the art.

EXAMPLES

Having generally described this invention, a further understanding can be obtained by reference to certain specific examples which are provided herein for purposes of illustration only and are not intended to be limiting unless otherwise specified.

Unless otherwise mentioned, "%" in the following Examples means "% by weight". Among the reaction results, conversion rate of the starting material was calculated from the measured acidic value, while yield of 1,4-CHDM was calculated from the analytical data in gas chromatography.

Example 1
Preparation of Catalyst

Activated carbon (CX-2 manufactured by Mitsubishi Chemical; particle size: 10–20 mesh) was heated in a 30% aqueous solution of nitric acid at 95° C. for three hours and filtered. Then it was washed with water and dried in vacuo (2 mmHg) at 80° C. for five hours. Water content in the resulting activated carbon was 0.95%.

$RuCl_3.3H_2O$ (1.578 g), 0.516 g of $H_2PtCl_6.6H_2O$ and 0.95 g of $SnCl_2.2H_2O$ were added to and dissolved in 3.6 ml of 5N aqueous solution of HCl. To this mixed solution were added 8.55 g of the above-prepared activated carbon. The solvent was evaporated therefrom in vacuo (25 mmHg) at 60° C. using an evaporator followed by drying at 150° C. for two hours together with an argon flow. After that, this was reduced in a hydrogen stream at 450° C. for two hours to give an activated carbon catalyst containing 6% of Ru, 2% of Pt and 5% of Sn.

Hydrogenation Reaction 1,4-Cyclohexanedicarboxylic acid (11.1 g; ratio of trans to cis being 0.30), 40 g of water and 2 g of the above catalyst were charged in a 200-ml autoclave of an inductively stirring type in an argon atmosphere. The temperature was raised to 230° C. under a hydrogen pressure of 1 MPa and, when the temperature reached 230° C., hydrogen was compressed thereinto to make the pressure 10 MPa so that the reaction was started. The reaction was carried out at a constant pressure for four hours and then the reaction solution was taken out. Conversion rate of the starting material and yield of 1,4-CHDM were determined for the reaction solution. The result was that the conversion rate was 99.3% and the yield of 1,4-CHDM was 91.8 molar %. A pseudo-first-order reaction rate constant during the reaction for one hour was calculated from the amount of absorbed hydrogen and was found to be 0.82/hr.

Example 2

An activated carbon catalyst containing 6% of Ru, 5% of Pt and 5% of Sn was prepared by the same method as in the preparation of the catalyst in Example 1. Hydrogenation reaction was carried out entirely in the same manner as in Example 1 except the use of the above catalyst whereupon the conversion rate was 99.1%, yield of 1,4-CHDM was 89.1 molar % and pseudo-first-order reaction rate constant was 0.53/hr.

Example 3

The same hydrogenation reaction as in Example 1 was carried out using the same catalyst as in Example 1 except that 20 g of water and 20 g of diglyme were used instead of 40 g of water. The result was that the conversion rate was 98.3% and the yield of 1,4-CHDM was 82.5%.

Example 4

An activated carbon catalyst containing 6% of Ru, 3% of Pt and 5% of Sn was prepared by the same method as in Example 1. The reduced catalyst (4 g), 15.2 g of 1,4-cyclohexanedicarboxylic acid (ratio of trans to cis being 0.30) and 35 g of water were charged in a 200-ml autoclave of an inductively stirring type in an argon atmosphere, the atmosphere was substituted with hydrogen and the temperature was raised up to 230° C. under a hydrogen pressure of 1 MPa. When that temperature was reached, hydrogen was compressed thereinto to an extent of 8.5 MPa and the reaction was carried out at a constant pressure for three hours. The result was that the conversion rate was 99.1% and the yield of 1,4-CHDM was 95.6%.

Example 5

The same hydrogenation reaction as in Example 4 was carried out except that 2 g of the same catalyst as in Example 4, 10 g of 1,4-cyclohexanedicarboxylic acid (the ratio of trans to cis being 0.30) and 40 g of water were used. The result is shown in Table 1.

Example 6

The same hydrogenation reaction as in Example 5 was carried out except that 0.5 g of $Na_2SO_4$ was added to the liquid phase of the hydrogenation reaction. The result is shown in Table 1.

Example 7

The same hydrogenation reaction as in Example 5 was carried out except that 1.0 g of $Na_2SO_4$ was added. The result is shown in Table 1.

Example 8

The same hydrogenation reaction as in Example 5 was carried out except that 8.0 g of $Na_2SO_4$ were added. The result is shown in Table 1.

Example 9

The same hydrogenation reaction as in Example 5 was carried out except that 1.0 g of KOH was added to the liquid phase of the hydrogenation reaction. The result is shown in Table 1.

TABLE 1

| Example | Catalyst Used | AMS or AEMS (g) | CR (mol %) | Yield (mol %) | PPRRC (/hr) | t/c ratio |
|---|---|---|---|---|---|---|
| 1 | 6% Ru-2% Pt-5% Sn/ active C | none | 99.3 | 91.8 | 0.82 | — |
| 2 | 6% Ru-5% Pt-5% Sn/ active C | none | 99.1 | 89.1 | 0.53 | — |
| 3 | 6% Ru-2% Pt-5% Sn/ active C | none | 98.3 | 82.5 | — | — |
| 4 | 6% Ru-3% Pt-5% Sn/ active C | none | 99.1 | 95.6 | — | — |
| 5 | | none | 98.8 | 81.6 | 0.65 | 1.51 |
| 6 | | $Na_2SO_4$(0.5) | 98.6 | 77.7 | 0.94 | 2.10 |
| 7 | | $Na_2SO_4$(1.0) | 98.8 | 77.1 | 0.80 | 2.18 |
| 8 | | $Na_2SO_4$(8.0) | 98.6 | 63.9 | 0.77 | 2.42 |
| 9 | | KOH(1.0) | 83.7 | 65.0 | 0.58 | 2.35 |

AMS or AEMS: Alkali metal salt or alkali earth metal salt
CR: Conversion rate of the starting material
Yield: Yield of 1,4-CHDM
PPRRC: Pseudo-first-order reaction rate
t/c: ratio of trans to cis in the resulting 1,4-CHDM

Example 10

The same hydrogenation reaction as in Example 4 was carried out except that 2 g of the same catalyst as in Example 4, 10 g of 1,4-cyclohexanedicarboxylic acid (ratio of trans to cis being 0.30) and 40 g of water were used and the hydrogenation temperature was 250° C. The result was that the conversion rate was 97.7% and the yield of 1,4-CHDM was 61.7 molar %. When quantitative determination of Ru, Pt and Sn in the reaction solution was carried out by means of an ICP-AES (inductively coupled plasma atomic emission spectrometry) in order to check the dissolution of the catalytic components, all metals were found to be below the measurable limits.

Comparative Example 1

An activated carbon catalyst containing 6% of Ru and 5% of Sn was prepared by the same method for preparing a catalyst as in Example 1 except that $H_2PtCl_6.6H_2O$ was not added. The same hydrogenation reaction as in Example 10 was carried out except that the above catalyst was used whereupon the converting rate was 81.2 molar % and the yield of 1,4-CHDM was 33.2 molar %. When quantitative determination of Ru and Sn in the reaction solution was carried out by means of an ICP-AES (inductively coupled plasma atomic emission spectrometry) in order to check the dissolution of the catalytic components, Ru was found to be below the measurable limit while 0.98% by weight of Sn was dissolved.

Example 11

Preparation of Catalyst

Activated carbon (CX-2 manufactured by Mitsubishi Chemical; particle size: 32–60 mesh) was heated at 95° C. for three hours in a 50% aqueous solution of nitric acid and filtered. After washing with water, it was dried in vacuo (2 mmHg) at 80° C. for five hours.

$H_2PtCl_6.6H_2O$ (0.956 g), 1.14 g of $SnCl_2.2H_2O$ and 1.863 g of $RuCl_3.3H_2O$ were added to and dissolved in 8.5 ml of water. Activated carbon (10.32 g) which was treated with nitric acid was added to and mixed with the above mixed solution, the solvent was evaporated at 60° C. in vacuo (25 mmHg) using an evaporator and the residue was dried at 150° C. for two hours in an argon stream. This was further reduced in a hydrogen stream at 450° C. for two hours to give an activated carbon catalyst containing 6% of Ru, 3% of Pt and 5% of Sn.

Hydrogenation Reaction 1,4-Cyclohexanedicarboxylic acid (ratio of trans to cis being 0.75) (15 g), 35 g of water and 4.2 g of the above-prepared catalyst were charged into a 200-ml autoclave of an inductively stirring type in an argon atmosphere. The temperature was raised up to 230° C. under a hydrogen pressure of 1 MPa and, when the temperature reached 230° C., hydrogen was compressed thereinto to an extent of 8.5 MPa and the reaction was started. The reaction was carried out at a constant pressure for three hours and, after completion of the reaction, only the reaction solution was taken out paying attention not to take out the precipitated catalyst and the conversion rate of starting material and the yield of 1,4-CHDM were measured.

To the catalyst remaining in the reactor were newly added 15 g of 1,4-cyclohexanedicarboxylic acid and 35 g of water and the reaction was carried out again under the same condition as above. This operation was repeated to conduct the reaction for six times in total. This catalyst was added to 300 ml of 1N ammonia solution followed by stirring for ten minutes. After stirring, the catalyst was filtered and repeatedly washed with water on a funnel until the pH of the filtrate became 8. The washed catalyst, 15 g of 1,4-cyclohexanedicarboxylic acid and 35 g of water were charged into an autoclave and subjected to the same reaction as above. The result of the reaction is shown in Table 2.

TABLE 2

| | | | Result of the Reaction | | |
|---|---|---|---|---|---|
| Example | Material for the Reaction | Base Species | 2nd Run | 6th Run | After treated with Base |
| 11 | 1,4-Cyclohexane dicarboxylic acid | $NH_3$ | Conversion Rate(%) 99.1 | 99.0 | 99.2 |
| | | | Yield of CHDM(%) 95.6 | 98.0 | 95.2 |
| | | | Rate Constant*[1] (/hr) 0.89 | 0.79 | 0.89 |

*[1]: Rate Constant: First-order rate constant during the primary reaction time for one hour When alicyclic carboxylic acid such as cycloalkyldicarboxylic acid or an alkyl ester thereof is hydrogenated using the catalyst of the present invention, conversion rate of the starting material and yield of cycloalkyldimethanol are particularly improved, dissolution of the catalytic metal components can be suppressed and, moreover, reaction rate can be improved as compared with the conventional method. Further, when the catalyst where the activity is reduced is treated with a solution containing a base, the activity can be effectively recovered whereby the catalyst can be regenerated. Thus, the present invention is highly valuable in an industrial utilization.

Obviously, numerous modifications and variations of the present invention are possible in light of the above teachings. It is therefore to be understood that within the scope of the appended claims, the invention may be practiced otherwise than as specifically described herein.

The priority documents of the present application, Japanese Patent Application No. 10-174386, filed Jun. 22, 1998, and Japanese Patent Application No. 10-226818, filed Aug. 11, 1998, are hereby incorporated by reference.

What is claimed is:

1. A process for making cycloalkyldimethanol, comprising:
   hydrogenating at least one starting compound selected from the group consisting of cycloalkyldicarboxylic acid and an alkyl ester thereof with hydrogen in a liquid phase in the presence of a catalyst and 0.1 to 80% by weight, relative to the starting compound, of an alkali metal salt or an alkaline earth metal salt at a temperature of from 150–240° C., to produce said cycloalkyldimethanol;
   wherein said catalyst comprises ruthenium, tin and platinum.

2. The process of claim 1, wherein the catalyst further comprises a carrier, and said ruthenium, tin and platinum are on said carrier.

3. The process of claim 2, wherein said carrier comprises carbon.

4. The process of claim 1, wherein said starting compound contains a cycloalkyl group containing 3–8 carbon atoms.

5. The process of claim 1, wherein said starting compound is 1,4-cyclohexanedicarboxylic acid or an ester thereof, and said cycloalkyldimethanol is 1,4-cyclohexanedimethanol.

6. The process of claim 1, wherein the molar ratio of said ruthenium:tin:platinum is 1:0.3–10:0.05–2.5.

7. The process of claim 1, wherein said hydrogenating is carried out in a solvent comprising water.

8. The process of claim 1, wherein said starting compound is 1,4-cyclohexanedicarboxylic acid.

9. The process of claim 1, wherein said starting compound contains an alkyl group containing 1–6 carbon atoms.

10. The process of claim 1, wherein said hydrogenating is carried out under a pressure of 0.1–30 MPa.

11. The process of claim 1, wherein said salt is selected from the group consisting of sodium sulfate, calcium hydroxide and potassium hydroxide.

12. The process of claim 1, wherein said salt is present in an amount of 0.5–20% by weight, based on the weight of said starting compound.

13. The process of claim 11, wherein said salt is present in an amount of 0.5–20% by weight, based on the weight of said starting compound.

14. The process of claim 1, wherein the amount of Pt is from 0.1–0.4 molar times that of the amount of Ru.

15. The process as claimed in claim 1, wherein said hydrogenation reaction is conducted at a pressure of between 1–25 MPa.

16. The process of claim 1, wherein said cycloalkyldimethanol has a trans/cis ratio of 1.51–2.42.

17. A method for regenerating a used catalyst, comprising:
   hydrogenating at least one starting compound selected from the group consisting of cycloalkyldicarboxylic acid and an alkyl ester thereof with hydrogen in a liquid phase in the presence of a catalyst comprising ruthenium, tin and platinum and 0.1 to 80% by weight, relative to the starting compound, of an alkali metal salt or an alkaline earth metal salt at a temperature of from 150–240° C., to produce cycloalkyldimethanol;
   obtaining the used catalyst from said hydrogenation and contacting said used catalyst with a base to regenerate said used catalyst.

18. A method for making cycloalkyldimethanol, comprising:
   hydrogenating at least one starting compound selected from the group consisting of cycloalkyldicarboxylic acid and an alkyl ester thereof with hydrogen in a liquid phase in the presence of a catalyst comprising ruthenium, tin and platinum and 0.1 to 80% by weight, relative to the starting compound, of an alkali metal salt or an alkaline earth metal salt at a temperature of from 150–240° C., to produce cycloalkyldimethanol;
   obtaining the used catalyst from said hydrogenation and contacting said used catalyst with a base to regenerate said used catalyst;
   hydrogenating at least one starting compound selected from the group consisting of cycloalkyldicarboxylic acid and an alkyl ester thereof with hydrogen in a liquid phase in the presence of the regenerated used catalyst and 0.1 to 80% by weight, relative to the starting compound, of an alkali metal salt or an alkaline earth metal salt at a temperature of from 150–240° C., to produce cycloalkyldimethanol.

* * * * *

UNITED STATES PATENT AND TRADEMARK OFFICE
CERTIFICATE OF CORRECTION

PATENT NO. : 6,294,703 B1  Page 1 of 1
DATED : September 25, 2001
INVENTOR(S) : Hara et al.

It is certified that error appears in the above-identified patent and that said Letters Patent is hereby corrected as shown below:

Title page,
Item [73], the Assignee's inforamtion should read:

-- [73]  Assignee: Mitsubishi Chemical Corporation, Tokyo (JP) --

Signed and Sealed this

Twenty-eighth Day of May, 2002

Attest:

Attesting Officer

JAMES E. ROGAN
Director of the United States Patent and Trademark Office